United States Patent [19]

Liu et al.

[11] Patent Number: 5,349,044
[45] Date of Patent: * Sep. 20, 1994

[54] POLYAMIDE MONOFILAMENT SUTURE MANUFACTURED FROM HIGHER ORDER POLYAMIDE

[75] Inventors: Cheng-Kung Liu, Norwalk; John C. Brewer, Bristol, both of Conn.

[73] Assignee: United States Surgical Corporation, Norwalk, Conn.

[ * ] Notice: The portion of the term of this patent subsequent to Jan. 18, 2011 has been disclaimed.

[21] Appl. No.: 126,679

[22] Filed: Sep. 24, 1993

Related U.S. Application Data

[63] Continuation of Ser. No. 828,005, Jan. 30, 1992, abandoned.

[51] Int. Cl.$^5$ .............................................. C08G 69/26
[52] U.S. Cl. .................................... 528/310; 528/323; 528/326; 528/335; 528/347; 606/228; 606/231
[58] Field of Search .............. 528/310, 323, 326, 335, 528/347; 606/231, 228

[56] References Cited

U.S. PATENT DOCUMENTS

| | | |
|---|---|---|
| 2,212,772 | 8/1940 | Graves . |
| 2,226,529 | 12/1940 | Austin . |
| 3,091,015 | 5/1963 | Zimmerman . |
| 3,124,632 | 3/1964 | Larkin et al. . |
| 3,156,750 | 11/1964 | Cuculo . |
| 3,303,169 | 2/1967 | Pitzl . |
| 3,311,691 | 3/1967 | Good . |
| 3,345,445 | 10/1967 | Siclari et al. . |
| 3,361,859 | 1/1968 | Cenzato . |
| 3,379,810 | 4/1968 | Ciceri et al. . |
| 3,436,450 | 4/1969 | Specker et al. . |
| 3,441,642 | 4/1969 | Engelman et al. . |
| 3,562,382 | 2/1971 | Fowler . |
| 3,577,500 | 4/1971 | Kohler et al. . |
| 3,739,055 | 6/1973 | Ueda et al. . |
| 3,792,010 | 2/1974 | Wasserman et al. . |
| 4,009,511 | 3/1977 | Gauntt . |
| 4,043,344 | 8/1977 | Landi et al. . |
| 4,047,533 | 9/1977 | Perciaccante et al. . |
| 4,338,277 | 7/1982 | Saito et al. . |
| 4,374,797 | 2/1983 | Koschinek et al. . |
| 4,446,299 | 5/1984 | Koschinek et al. . |
| 4,461,740 | 7/1984 | Koschinek et al. . |
| 4,470,941 | 9/1984 | Kurtz .................. 428/397 |
| 4,504,432 | 3/1985 | Kamei et al. . |
| 4,504,545 | 3/1985 | Kurita et al. . |
| 4,542,063 | 9/1985 | Tanji et al. . |
| 4,550,730 | 11/1985 | Shalaby et al. ............. 528/295 |
| 4,578,451 | 3/1986 | Weaver et al. . |
| 4,621,021 | 11/1986 | Kitamura et al. . |
| 4,624,816 | 11/1986 | Kurita et al. . |
| 4,701,377 | 10/1987 | Kurita et al. . |
| 4,758,472 | 7/1988 | Kitamura et al. . |
| 4,839,132 | 7/1989 | Wang . |
| 4,859,389 | 8/1989 | Kurita et al. .................. 264/130 |
| 5,007,922 | 4/1991 | Chen et al. ................... 606/228 |
| 5,102,419 | 4/1992 | Gertzman et al. . |
| 5,102,420 | 4/1992 | Hunter et al. ................. 606/231 |
| 5,147,382 | 9/1992 | Gertzman et al. . |
| 5,156,788 | 10/1992 | Chesterfield et al. . |
| 5,217,485 | 6/1993 | Liu et al. ..................... 606/228 |
| 5,225,485 | 7/1993 | Liu et al. ..................... 606/230 |
| 5,279,783 | 1/1994 | Liu et al. ..................... 606/228 |

FOREIGN PATENT DOCUMENTS

| | | |
|---|---|---|
| 0132131 | 1/1985 | European Pat. Off. . |
| 0415783 | 3/1991 | European Pat. Off. . |
| 0423807 | 4/1991 | European Pat. Off. . |
| 0526759 | 2/1993 | European Pat. Off. . |
| 0553883 | 8/1993 | European Pat. Off. . |
| 3216005 | 11/1983 | Fed. Rep. of Germany . |
| 3319953 | 12/1983 | Fed. Rep. of Germany . |
| 53-24417 | 3/1978 | Japan . |
| 54-27023 | 3/1979 | Japan . |
| 57-139513 | 8/1982 | Japan . |
| 59-157314 | 9/1984 | Japan . |

OTHER PUBLICATIONS

Search Report form European Appln. No. 93101510.1 dated Jun. 8, 1993.
U.S. patent application Ser. No. 07/828,010, filed Jan. 30, 1992.

*Primary Examiner*—John Kight, III
*Assistant Examiner*—P. Hampton-Hightower

[57] ABSTRACT

A higher order polyamide monofilament suture exhibits improved properties such as greater resistance to creep, greater knot security and greater chemical stability in aqueous environments.

18 Claims, 1 Drawing Sheet

POLYAMIDE MONOFILAMENT SUTURE MANUFACTURED FROM HIGHER ORDER POLYAMIDE

This is a continuation of copending application Ser. No. 07/828,005 filed on Jan. 30, 1992, now abandoned.

BACKGROUND OF THE INVENTION

This invention relates to a polyamide (nylon) monofilament suture and, more particularly, to such a suture manufactured from a higher order polyamide such as nylon 12.

Polyamide monofilament sutures are known. Illustrative of the known processes for the melt spinning of polyamide strands (filament,yarn, etc.) are those described in U.S. Pat. Nos. 2,212,772; 2,226,549; 3,091,016; 3,303,169; 3,345,445; 3,361,859; 3,379,810; 3,382,307; 3,577,500; 4,009,511; 4,374,797; 4,446,299; 4,461,740; 4,504,432; 4,504,545; 4,542,063; 4,578,421; 4,621,021; 4,624,816; 4,701,377; 4,758,472; 4,839,132; and, 4,859,389.

One important characteristic of a suture is the amount of effort typically required to straighten the suture upon its removal from the package in order to ready the suture for use. In the case of a polyamide monofilament suture, this effort appears to be related to the "energy" of the suture, i.e., the integrations of the stress-strain curve for the suture measured in kilograms, and is equivalent to the work expended in elongating the monofilament by a specified percentage of its original length. As the energy of a given size of polyamide monofilament suture is less so, too, the amount of effort required to straighten the suture prior to use is less.

Another important consideration in the manufacture and use of sutures is that a yarn may stretch when under tension for an extended period of time. Under the tension of a surgeon's knot used for wound closure, a suture may undergo stretching which will cause the ligature to loosen, a phenomenon referred to herein as "creep".

Commonly owned copending U.S. patent application Ser. No. 07/828,010 filed Jan. 30, 1992 describes a process for manufacturing a polyamide monofilament suture from such nylons as nylon 6 and nylon 6,6 which exhibits reduced energy and/or an increased ability to retain a knot for a given suture when compared to prior polyamide sutures.

The present invention provides a suture exhibiting excellent dimensional stability, or resistance to creep, and high levels of strength retention and chemical stability when exposed to aqueous environments. The present invention further provides a suture exhibiting increased knot security or stability.

SUMMARY OF THE INVENTION

In accordance with the present invention, there is provided a polyamide monofilament suture manufactured from a higher order polyamide, i.e, a fiber-forming polyamide homopolymer or copolymer possessing a substantial number of repeating units selected from the group consisting of units of the structure

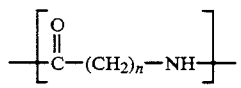

in which n is at least about 7 and units of the structure

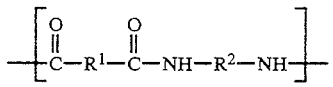

in which $R^1$ is an aliphatic group of from about 4 to about 20 carbon atoms, a cycloaliphatic group of from about 6 to about 20 carbon atoms or an aromatic group of from about 6 to about 20 carbon atoms and $R^2$ is an aliphatic, cycloaliphatic or aromatic group of from about 6 to about 20 carbon atoms, provided, $R^1$ contains at least 6 carbon atoms when $R^2$ is an aliphatic group of 6 carbon atoms or $R^2$ contains at least 8 carbon atoms when $R^1$ contains 4 carbon atoms.

BRIEF DESCRIPTION OF THE DRAWINGS

FIG. 1A is a schematic illustration of apparatus which is suitable for manufacturing the high order polyamide monofilament suture of this invention; and, FIG. 1B is a modification of the apparatus of FIG. 1A which is particularly suitable for the manufacture of polyamide monofilaments of smaller size, e.g., sizes 4/0 and smaller.

DESCRIPTION OF THE PREFERRED EMBODIMENTS

The preferred higher order polyamides from which the suture of this invention can be manufactured contain at least about 30 mole percent, preferably at least about 50 mole percent and most preferably at least about 70 mole percent of units of the structure

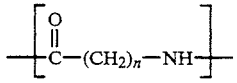

and/or the structure

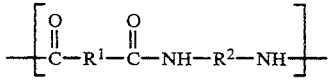

in which m, $R^1$ and $R^2$ have the above-designated meanings.

The higher order fiber-forming polyamides can be prepared by polymerizing aminocarboxylic acid and/or corresponding lactam or by polymerizing substantially equimolar proportions of diamine and dicarboxylic acid or functional derivative thereof such as an ester or acid chloride employing known and conventional techniques. Examples of the aforementioned aminocarboxylic acids or lactams thereof which are useful in preparing the higher order polyamides include those compounds containing at least about 8, preferably at least about 10 and most preferably at least about 12 carbon atoms. Particular examples of useful aminocarboxylic acids and lactams include capryllactam, 10-aminodecanoic acid, 11-aminoundecanoic acid and laurolactam, and the like.

Diamines suitable for use in preparation of the higher order fiber-forming polyamides include the straight chain and branched chain alkyl, aryl and alkaryl diamines. Such diamines include, e.g., those represented by the general formula

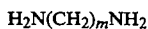

wherein m is an integer of at least about 6 and preferably at least about 12. Suitable diamines include hexamethylene diamine, octamethylene diamine, trimethylhexamethylene diamine, m-phenylene diamene and m-xylylene diamine.

The useful dicarboxylic acids can be represented by the formula

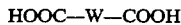

wherein W is a divalent aliphatic or aromatic group containing at least 6 carbon atoms. Suitable aliphatic acids include sebacic acid, suberic acid, azelaic acid, pimellic acid and adipic acid. Suitable aromatic acids include isophthalic acid and terephthalic acid.

Typical examples of the polyamide or nylon (as it is often called) resin used in the present invention are nylon 11, 12, 6/9, 6/12 and other higher order polyamides. Nylon 12 is an especially preferred fiber-forming polyamide resin from which the suture of this invention can be manufactured. In general, useful higher order polyamides will possess a number average molecular weight of at least about 10,000 and a melt flow index in g/10 min. of from about 1.5 to about 7.5.

Also included are block and random copolymers formed from one or more of the foregoing monomers and one or more other monomers copolymerizable therewith, e.g., lactones, alpha-hydroxy carboxylic acids and oligomers thereof, aminocarboxylic acids and/or corresponding lactams in addition to those mentioned, etc. Suitable lactones include gamma-butyrolactone and epsilon caprolactone. Suitable alpha-hydroxy carboxylic acids include hydroxybutanoic acid and hydroxycaproic acid. Useful higher order polyamides also include any of the foregoing homopolymers and copolymers blended with one or more compatible polymers, e.g., unlimited amounts of other polyamide homopolymers and/or polyamide copolymers, relatively minor amounts of polyester homopolymers and/or polyester copolymers, polyurethanes, etc.

A suitable process for the manufacture of the higher order polyamide monofilament suture of the present invention is disclosed and claimed in commonly assigned, concurrently filed U.S. patent application Ser. No. 07/828,010, filed Jan. 30, 1992, the contents of which are incorporated by reference herein. The process comprises the operations of extruding the polyamide resin at an extrusion temperature of from about 180° to about 290° C. to provide a monofilament, stretching the solidified monofilament at a temperature of from about 40° to about 98° C. in water (or other suitable liquid medium) or at from about 50° to about 185° C. in air (or other suitable gaseous medium) at a stretch ratio of from about 3:1 to about 5:1 to provide a stretched monofilament and annealing (relaxing) the stretched monofilament at a temperature of from about 100° to about 240° C. to provide the finished suture, the annealing resulting in shrinkage of the stretched monofilament for a recovery to within about 80% to about 97% of the length of the monofilament prior to annealing.

FIG. 1A schematically illustrates a higher order polyamide monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polyamide resin are introduced to the extruder through hopper 12. Any of the polyamides which are useful for the formation of fibers can be used herein. Representative of such polyamides are polycaprolactam (nylon 6) and polyhexamethylene adipamide (nylon 6,6). Optionally, the polyamide sutured may be dyed.

Motor-driven metering pump 13 delivers extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 and preferably from about 1 to about 20 cm. If desired, a chimney (not shown), or shield, can be provided to reduce the length of air gap, e.g., to from 1 to 10 cm, thereby isolating monofilament 16 from contact by air currents which might otherwise affect the cooling of the monofilament in some unpredictable manner. In general, barrel zone A of the extruder can be maintained at a temperature of from about 215° to 225° C., zone B at from about 220° to 230° C. and zone C at from about 220° to about 235° C. Additional temperature parameters include: metering pump block 13 at from about 220° to about 235° C., spin pack 14 at from about 215° to about 235° C., spinneret 15 at from about 215° to about 235° C. and quench bath at from about 35° to about 45° C.

Entering quench bath 17, monofilament 16 is passed by driven roller 18 over rollers 19 and 20 and thereafter is wrapped around a first godet 21 provided with nip roll 22 to prevent slippage which might otherwise result from the subsequent stretching operation. Monofilament 16 passing from godet 21 is stretched, e.g., with stretch ratios on the order of from about 3:1 to about 5:1 and preferably from about 3.5:1 to about 4.5:1, to effect its orientation and thereby increase its tensile strength. In the stretching operation shown in FIG. 1A, generally suitable for larger size sutures, e.g., sizes 2/0 to 3/0, monofilament 16 is drawn through hot water draw bath 23 by means of second godet 24 which rotates at a higher speed than first godet 21 to provide the desired stretch ratio. The temperature of hot water draw bath 23 is advantageously from about 60° to about 98° C. and preferably is from about 80° to about 95° C.

In the alternative stretching operation shown in FIG. 1B, generally preferred for smaller sutures sizes, e.g., sizes 4/0 to 8/0, monofilament 16 is drawn by second godet 24' through hot air oven chamber 23' at a temperature of from about 100° to about 185° C. and preferably from about 150° to about 170° C. to provide the desired amount of stretch. Following the stretching operation shown in FIGS. 1A or 1B, monofilament 16 is subjected to an on-line annealing (relaxation) operation as a result of which the monofilament shrinks. In the processes of FIGS. 1A and 1B, annealing (relaxation) is accomplished by driving monofilament 16 by third godet 26 through second hot air oven chamber 25 at a temperature of from about 120° to about 180° C. and preferably from about 140° to about 160° C. At these temperatures, monofilament 16 will generally recover to within about 85 to about 97 percent, and preferably to within about 95 percent, of its pre-annealed length to provide the finished suture. The third godet relates at a slower speed than the second godet thus relieving tension on the filament.

If desired, the suture can be dyed. If transportation in bulk is required after dyeing, it is preferable to collect the dyed monofilaments in skeins, not on spools, as the latter can cause damage to the suture (flattening). Logwood extract is a known dye for polyamide sutures and can be used herein. However, other dyes known to be suitable for incorporation in sutures can also be used herein, e.g., D&C Green No. 5 and D&C Blue No. 2 as described in the *Handbook of U.S. Colorants for Food, Drugs and Cosmetics*, by Daniel M. Marrion, 1979.

It is believed that the superior physical and chemical properties of the polyamide sutures of the present invention are due at least in part to the increased carbon content in the structural units of the higher order polyamide resins used in their manufacture. This results in a decrease in the number of amide linkages in the resin. The hydrophilic amide linkage is not only susceptible to cleavage in an aqueous environment, it also favors hydrogen bonding and consequently an affinity for attracting water to the polymer.

In order that those skilled in the art may be better able to practice the present invention, the following examples are given as an illustration of the preparation and superior characteristics of the polyamide sutures of the present invention. It should be noted that the invention is not limited to the specific details embodied in the examples and further that all parts are be weight.

EXAMPLES 1–3

Table I below sets forth typical conditions for extruding, stretching and annealing (relaxing) various sizes of polyamide monofilament suture in accordance with this invention. All of the monofilament sutures were fabricated from AESNO (a commercially available nylon 12 from ATOCHEM North America, Inc.) having an inherent viscosity of about 1.6 dl/g and a moisture content of less than 0.08 weight percent, and a melt flow index of 3.4 g/10 min. as indicated by the manufacturer.

TABLE I

CONDITIONS OF MANUFACTURING VARIOUS SIZES OF HIGHER ORDER POLYAMIDE MONOFILAMENT SUTURE

| Example | 1 | 2 | 3 |
|---|---|---|---|
| Suture Size | 0 | 3/0 | 6/0 |
| Process Conditions | Extrusion Operation | | |
| extruder screw, rpm | 24 | 10.8 | 3.4 |
| pump rpm | 17.4 | 6.8 | 9.85 |
| driven roller, rpm | 7 | 7 | 8 |
| barrel temp., °C., zone A | 200 | 200 | 200 |
| barrel temp., °C., zone B | 210 | 210 | 210 |
| barrel temp., °C., zone C | 220 | 215 | 215 |
| clamp temp., °C. | 215 | 215 | 215 |
| adapter temp., °C. | 215 | 215 | 215 |
| pump temp., °C. | 220 | 218 | 222 |
| block temp., °C. | 220 | 218 | 218 |
| barrel melt temp., °C. | 218 | 215 | 214 |
| pump melt temp., °C. | 228 | 221 | 218 |
| spinneret melt temp., °C. | 230 | 225 | 226 |
| barrel pressure, psi | 1800 | 2150 | 2350 |
| pump pressure, psi | 1100 | 1484 | 2650 |
| spinneret pressure, psi | 4500 | 3228 | 2650 |
| pump size, cc per revolution | 1.168 | 1.168 | 0.16 |
| diameter of spinneret orifices, mm | 1.25 | 1.25 | 0.5 |
| no. of spinneret orifices | 4 | 4 | 4 |
| air gap, cm | 3 | 2 | 3 |
| quench bath temp., °C. | 30 | 36 | 30 |
| depth of driven roller | 38 | 37 | 38 |
| filtration, microns | 12 | 12 | 12 |
| Stretching (Orienting) Operation | | | |
| draw bath temp, °C. | 97 | 97 | — |
| first oven chamber temp, °C. | 98 | 82 | 135 |
| first godet, mpm | 10.3 | 10.3 | 11.6 |
| second godet, mpm | 40.7 | 40.8 | 45.4 |
| draw ratio | 4.1 | 4.1 | 4.1 |
| Annealing (Relaxing) Operation | | | |
| second oven chamber temp, °C. | 98 | 98 | 98 |
| third godet, mpm | 39.0 | 38.9 | 43.4 |

COMPARATIVE EXAMPLE 1

Table II below sets forth typical conditions for extruding, stretching and annealing (relaxing) a size 3/0 polyamide 6 monofilament suture. In general, useful polyamides will possess a number average molecular weight of at least about 15,000 and a melt flow index in g/10 min of from about 3 to about 8 and preferred from about 4 to about 6. The suture was manufactured from Capron 8207F (Allied Signal Corp.), a polycaprolactone having a relative viscosity of 73.9 and a moisture content of 0.062 weight percent as indicated by the manufacturer.

TABLE II

CONDITIONS OF MANUFACTURING A POLYAMIDE 6 MONOFILAMENT SUTURE

| Comparative Example | 1 |
|---|---|
| Suture Size | 3/0 |
| Process Conditions | Extrusion Operation |
| extruder screw, rpm | 22.0 |
| pump rpm | 7.65 |
| driven roller, rpm | 10 |
| barrel temp., °C., zone A | 220 |
| barrel temp., °C., zone B | 225 |
| barrel temp., °C., zone C | 230 |
| clamp temp., °C. | 225 |
| adapter temp., °C. | 225 |
| pump temp., °C. | 225 |
| block temp., °C. | 225 |
| spinneret temp., °C. | 230 |
| barrel melt temp., °C. | 234 |
| pump melt temp., °C. | 230 |
| spinneret melt temp., °C. | 227 |
| barrel pressure, psi | 2650 |
| pump pressure, psi | 2890 |
| spinneret pressure, psi | 2730 |
| pump size, cc per revolution | 1.168 |
| diameter of spinneret orifices, mm | 1.25 |
| no. of spinneret orifices | 4 |
| air gap, cm | 2 |
| quench bath temp., °C. | 45 |
| depth of driven roller | 25 |
| filtration, microns | 12 |
| Stretching (Orienting) Operation | |
| draw bath temp, °C. | 80 |
| first oven chamber temp, °C. | — |
| first godet, mpm | 17.6 |
| second godet, mpm | 70.1 |
| draw ratio | 4.0 |
| Annealing (Relaxing) | |

TABLE II-continued

CONDITIONS OF MANUFACTURING A
POLYAMIDE 6 MONOFILAMENT SUTURE

| Comparative Example | 1 |
|---|---|
| Suture Size | 3/0 |

| | Operation |
|---|---|
| second oven chamber temp, °C. | 150 |
| third godet, mpm | 66.4 |

COMPARATIVE EXAMPLE 2

A size 3/0 nylon 6 suture was prepared in the matter of Comparative Example 1 except that the suture was dyed with black logwood extract.

The physical properties of the higher order polyamide monofilament sutures of this invention and those of the comparative examples were measured at 73° F. and 50 relative humidity. Measurements of percent elongation, tensile strength and energy were carried out employing an Instron Corporation (Canton, Mass.) Tensile Tester, model no. 4301, equipped with yarn grips and operated with a gauge length of 127 mm and a crosshead speed of 127 mm/min.

The physical properties of the sutures and the procedures employed for their measurement are set forth in Table III as follows:

TABLE III

PROCEDURES FOR MEASURING PHYSICAL PROPERTIES OF POLYAMIDE MONOFILAMENT SUTURES

| Physical Property | Test Procedure |
|---|---|
| knot pull, tensile strength, kg | U.S.P. XXI, tensile strength, sutures (881) |
| straight pull, kg | ASTM D-2256, Instron Corporation |
| elongation at break, % | ASTM D-2256 |
| tensile strength, kg/mm² | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength for 2/0 nonabsorbable sutures (n = 10 loops per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. Each pass of the cloth across the knot (for a total of 100 passes), the knot is inspected for top throw security. For a knot to be considered secure, the 3 mm ears must not come undone and there must be no relaxation of the knot or loss of the fourth throw. |
| melt flow | ASTM D-1238 |

Table IV below sets forth the physical properties of the size 3/0 polyamide 12 suture of the present invention as compared to those properties of the polyamide 6 suture employing the physical testing procedure set forth in Table II.

TABLE IV

| Physical Property | Comp. Ex. 1 | Comp. Ex. 2 | Ex. 1 | Ex. 2 |
|---|---|---|---|---|
| Wet strength retention | 80% | 81% | 105% | 99% |
| for knot-pull | | | | |
| Wet strength retention | 94% | 83% | 100% | 100% |
| for straight-pull | | | | |
| Diameter change | +5% | 0% | +1% | −1% |
| Modulus change | −49% | −32% | −5% | −6% |
| diameter (mm) | 0.230 | 0.236 | 0.242 | 0.244 |
| Wet diameter (mm) | 0.241 | 0.236 | 0.245 | 0.242 |
| knot-pull (kg) | 1.78 | 1.63 | 1.48 | 1.63 |
| Wet knot-pull (kg) | 1.42 | 1.32 | 1.55 | 1.61 |
| Straight-pull (kg) | 2.09 | 2.01 | 2.07 | 1.83 |
| wet straight-pull (kg) | 1.97 | 1.68 | 2.09 | 1.85 |
| Energy 0–5% (kg-mm) | 1.04 | 1.30 | 2.50 | 2.18 |
| Wet Energy 0–5% (kg-mm) | 0.24 | 0.42 | 2.69 | 1.70 |
| Energy 0–10% (kg-mm) | 6.56 | 3.70 | 10.93 | 8.53 |
| Wet Energy 0–10% (kg-mm) | 3.55 | 2.71 | 11.00 | 7.51 |

As demonstrated in Table IV, the strength retention for both straight pull and knot-pull of the nylon 12 suture when exposed to an aqueous medium containing large quantities of water is much greater than that of a corresponding nylon 6.

The yarn of Example 2 and Comparative Example 2 were placed under 1.8 g/den constant tension in a water bath at ambient temperature. At the time intervals listed below, the percent elongation, or "creep", was measured. Table V further illustrates the physical stability of the nylon 12 suture.

TABLE V

| Creep, % | Nylon 6 Comparative Example 2 | Nylon 12 Example 2 |
|---|---|---|
| 5 min | 3.3% | 1.1% |
| 10 min | 4.4% | 1.1% |
| 30 min | 6.1% | 1.7% |
| 45 min | 7.2% | 1.7% |
| 18 hours | 13.2% | 2.9% |

Table V further illustrates the physical stability of the nylon 12 suture.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A polyamide monofilament suture manufactured from a fiber-forming polyamide homopolymer or copolymer possessing a substantial number of units selected from the group consisting of units of the structure in which n is at

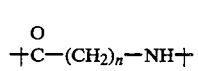

at least about 7 and units of the structure

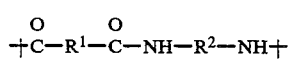

in which $R^1$ is an aliphatic group of from about 4 to about 20 carbon atoms, a cycloaliphatic group of from about 6 to about 20 carbon atoms or an aromatic group of from about 6 to about 20 carbon atoms and $R^2$ is an aliphatic, cycloaliphatic or aromatic group of from about 6 to about 20 carbon atoms, provided, $R^1$ contains at least 6 carbon atoms when $R^2$ is an aliphatic group of 6 carbon atoms or $R^2$ contains at least 8 carbon atoms when $R^1$ contains 4 carbon atoms, provided, that where the polyamide is a copolymer, any units other than the aforesaid units which may be present contain a carbonyl, the suture being manufactured from the polyamide by an extrusion process which comprises the steps of extruding the polyamide resin at an extrusion temperature of from about 180° to about 290° C. to provide a monofilament, stretching the solidified monofilament at a temperature of from about 40° to about 98° C. in liquid medium or at from about 50° to about 185° C. in gaseous medium at a stretch ratio of from about 3:1 to about 5:1 to provide a stretched monofilament and annealing the stretched monofilament at a temperature of from about 100° to about 240° C. to provide the finished suture, the annealing resulting in shrinkage of the stretched monofilament for a recovery to within about 80% to about 97% of the length of the monofilament prior to annealing, said monofilament having a decreased 0–5% energy compared to a cold-drawn monofilament of the same size and composition.

2. The suture of claim 1 wherein the polyamide contains at least about 30 mole percent of the units.

3. The suture of claim 1 wherein the polyamide contains at least about 50 mole percent of the units.

4. The suture of claim 1 wherein the polyamide contains at least about 70 mole percent of the units.

5. The suture of claim 1 wherein $R^1$ is about $C_4$ aliphatic and $R^2$ is about $C_{10}$ aliphatic.

6. The suture of claim 1 wherein $R^1$ is about $C_4$ aliphatic and $R^2$ is about $C_{12}$ aliphatic.

7. The suture of claim 1 wherein $R^1$ is about $C_8$ aliphatic and $R^2$ is about $C_8$ aliphatic.

8. The suture of claim 7 wherein $R^1$ is about $C_6$ aliphatic and $R^2$ is about $C_{4-8}$ aliphatic.

9. The suture of claim 1 wherein $R^1$ is about $C_6$ aliphatic and $R^2$ is about $C_{12}$ aliphatic.

10. The suture of claim 1 containing up to about 1 percent by weight of material selected from the group consisting of dyes and pigments.

11. The suture of claim 1 wherein the units containing a carbonyl are derived from at least one member selected from the group consisting of lactone, alpha-hydroxy carboxylic acid, oligomer of alpha-hydroxy carboxylic acid, aminocarboxylic acid and lactam.

12. The suture of claim 1 exhibiting not more than about 6 percent creep in an aqueous medium under 1.8 g/den tension.

13. The suture of claim 1 exhibiting at least about 85 percent wet strength retention for knot pull.

14. The suture of claim 1 exhibiting at least about 95 percent wet strength retention for straight pull.

15. A polyamide monofilament suture manufactured from nylon 12, the suture being manufactured by an extrusion process which comprises the steps of extruding the nylon 12 resin at an extrusion temperature of from about 180° to about 290° C. to provide a monofilament, stretching the solidified monofilament at a temperature of from about 40° to about 98° C. in liquid medium or at from about 50° to about 185° C. in gaseous medium at a stretch ratio of from about 3:1 to about 5:1 to provide a stretched monofilament and annealing the stretched monofilament at a temperature of from about 100° to about 240° C. to provide the finished suture, the annealing resulting in shrinkage of the stretched monofilament for a recovery to within about 80% to about 97% of the length of the monofilament prior to annealing, said monofilament having a decreased 0–5% energy compared to a cold-drawn nylon 12 monofilament of the same size.

16. The suture of claim 15 exhibiting not more than about 6 percent creep in an aqueous medium under 1.8 g/den tension.

17. The suture of claim 15 exhibiting at least about 85 percent wet strength retention for knot pull.

18. The suture of claim 15 exhibiting at least about 95 percent wet strength retention for straight pull.

* * * * *